(12) United States Patent
Maschke

(10) Patent No.: US 8,662,085 B2
(45) Date of Patent: Mar. 4, 2014

(54) MAGNETIC NANOPARTICLE AND GROUP OF NANOPARTICLES

(75) Inventor: Michael Maschke, Lonnerstadt (DE)

(73) Assignee: Siemens Aktiengesellschaft, München (DE)

( * ) Notice: Subject to any disclaimer, the term of this patent is extended or adjusted under 35 U.S.C. 154(b) by 234 days.

(21) Appl. No.: 13/036,065

(22) Filed: Feb. 28, 2011

(65) Prior Publication Data

US 2011/0218380 A1    Sep. 8, 2011

(30) Foreign Application Priority Data

Mar. 2, 2010 (DE) .......................... 10 2010 009 883

(51) Int. Cl.
*A61B 19/00* (2006.01)
(52) U.S. Cl.
USPC ........................................................ 128/899
(58) Field of Classification Search
USPC ............... 128/899; 600/9–15, 411; 424/9.322
See application file for complete search history.

(56) References Cited

U.S. PATENT DOCUMENTS

| | | | |
|---|---|---|---|
| 5,843,780 A | 12/1998 | Thomson | |
| 6,514,481 B1 | 2/2003 | Prasad et al. | |
| 2005/0090732 A1* | 4/2005 | Ivkov et al. | 600/411 |
| 2006/0024231 A1* | 2/2006 | Schnitzer et al. | 424/1.49 |
| 2008/0306324 A1* | 12/2008 | Bonutti et al. | 600/12 |
| 2009/0148387 A1 | 6/2009 | Bikram | |
| 2009/0234220 A1 | 9/2009 | Maschke | |
| 2010/0080788 A1* | 4/2010 | Barnett et al. | 424/94.5 |

FOREIGN PATENT DOCUMENTS

WO    WO 2005059118 A2    6/2005

OTHER PUBLICATIONS

Gamarra et al., "In vitro study of CD133 human stem cells labeled with superparamagnetic iron oxide nanoparticles", Nanomedicine: Nanotechnology, Biology and Medicine 4, 2008, pp. 330-339, Elsevier Inc.
Cheung et al., "Cell Number Quantification of USPIO-labeld Stem Cells by MRI: An in Vitro Study", Engineering in Medicine and Biology Society, 2006.EMBS '06. 28th Annual International Conference of the IEEE, Aug. 30-Sep. 3, 2006, pp. 476-479.
Belicchi et al., "Some application of nanotechnologies in stem cells research", Materials Science and Engineering B 165, 2009, pp. 139-147.
Arampatzis et al., "Cell Transplantation for Myocardial Repair: Current Perspectives, Initial Experience in Humans, and Future Directions", Euro PCR, May 2004, pp. 214-231, Erasmus Medical Centre, Thorax Centre, Rotterdam, The Netherlands.

* cited by examiner

*Primary Examiner* — Christine Matthews

(57) ABSTRACT

For particularly effective stem cell therapy a nanoparticle is provided. The nanoparticle has a first element consisting of a magnetic material, a support or envelope element consisting of a biodegradable material, a first substance containing an x-ray contrast agent, and a second substance containing stem cells. The stem cells are embodied such that they can be used for angiogenesis or for myogenesis.

8 Claims, 2 Drawing Sheets

MAGNETIC NANOPARTICLE AND GROUP OF NANOPARTICLES

CROSS-REFERENCE TO RELATED APPLICATIONS

This application claims priority of German application No. 10 2010 009 883.2 filed Mar. 2, 2010, which is incorporated by reference herein in its entirety.

FIELD OF THE INVENTION

The invention relates to a magnetic nanoparticle and a group of nanoparticles as well as a method for positioning nanoparticles.

BACKGROUND OF THE INVENTION

One of the most frequent diseases with a fatal outcome is vascular disease, which can lead to heart attacks or strokes for example. Heart attacks are caused by disease of the coronary vessels, whereby arteriosclerotic plaque results in thrombocyte activation and thus formation of a local thrombus. This can lead to a total occlusion of coronary vessels and thus to a blockage of the blood flow. Occlusion in the case of a heart attack is nowadays in the majority of cases treated by a PCTA (Percutaneous Transluminal Coronary Angioplasty). To this end the narrow points of the coronary vessels are expanded using a "balloon catheter". However, as a result of this treatment myocardial muscle tissue that is already dead (necrotic tissue) is unable to regenerate again.

Around 2001 the first experiments on regenerating tissue in the heart were performed. The first attempts were limited to the introduction of body cells, e.g. stem cells, into the coronary vessel system. This method is called angiogenesis. Document U.S. Pat. No. 5,843,780 A1 discloses the preparation of stem cells. For the angiogenesis a balloon catheter is introduced into the section of vessel to be treated and the blood flow in the vessel is interrupted briefly by inflating the balloon. A solution containing stem cells is introduced into the closed vessel by a lumen in the catheter under high pressure. In comparative studies an improvement in pumping performance was identified. Since a very large quantity of body cells has to be produced in bioreactors for this treatment, this kind of treatment has not become widespread. The treatment known as myogenesis has gained higher acceptance, whereby body cells are injected directly into the myocardial muscle, advantageously in the area of the infarction scar, and there form new muscle cells which increase the pumping function of the heart. Initially the cells were introduced by surgical intervention by opening the thorax. Since this very intensive intervention (heart-lung machine) is associated with many risks, the minimally invasive injection of body cells into the myocardial muscle using special catheters and needles has become widespread.

US 2009/0234220 discloses a catheter with which stem cells can be injected. A disadvantage of all current methods is that the stem cells are transported by blood circulation away from the vessel, vessel section or organ to be treated and only a few stem cells remain at the desired location for angiogenesis or myogenesis.

SUMMARY OF THE INVENTION

It is the object of the present invention to create an opportunity for introducing stem cells into the body of a living being without their immediately being transported away from the organ to be treated by blood circulation.

The object is achieved inventively by a magnetic nanoparticle and a group of nanoparticles as well as by a method for positioning nanoparticles as claimed in the independent claims. Advantageous embodiments of the invention are respectively the subject matter of the associated dependent claims.

The inventive nanoparticle has a first element consisting of a magnetic material, a support or envelope element consisting of a biodegradable material, a first substance containing an x-ray contrast agent, and a second substance containing stem cells, wherein the stem cells are embodied such that they can be used for angiogenesis or for myogenesis. Such inventive nanoparticles can for example as a result of the magnetic material be held and concentrated at a desired treatment location by means of a magnetic field, so that few if any are transported away, for example by blood circulation. The stem cells can thereby be used in concentrated form at the intended treatment location and are thereby especially effective. The stem cells can thus be applied locally in defined fashion. As a result of the x-ray contrast agent likewise contained the nanoparticles are simultaneously easily visible in the x-ray or angiography image, so that it is easily possible to monitor and check the position of the nanoparticles. The biodegradable material can moreover contribute a temporal component in respect of the release of the stem cells.

The inventive group or the cluster of nanoparticles, formed from at least three nanoparticles, has a first element consisting of a magnetic material, a support or envelope element consisting of a biodegradable material, a first substance containing an x-ray contrast agent, and a second substance containing stem cells, whereby the stem cells are embodied such that they can be used for angiogenesis or for myogenesis. Such inventive nanoparticle groups can for example as a result of the magnetic material be held and concentrated at a desired treatment location by means of a magnetic field, so that few if any are transported away, for example by blood circulation. The stem cells can thereby be used in concentrated form at the intended treatment location and are thereby especially effective. The stem cells can thus be applied locally in defined fashion. As a result of the x-ray contrast agent likewise contained the nanoparticle groups are simultaneously easily visible in the x-ray or angiography image, so that it is easily possible to monitor and check the position of the nanoparticle group. The biodegradable material can moreover contribute a temporal component in respect of the release of the stem cells.

According to one embodiment of the invention the individual nanoparticles each have an average diameter of between 5 nm and 300 nm. They are thus small enough to diffuse into the body tissue and large enough to react to a magnetic field. Preferably the diameters of the nanoparticles are between 50 nm and 100 nm, ideally approximately 80 nm. Larger nanoparticles are also possible.

Advantageously the first element is embodied as a core element. According to a further embodiment of the invention the support or envelope element is embodied as an envelope enclosing the first element, the first substance and the second substance. In this way biocompatibility can be exploited, in order to determine the precise time of release of the active agents, thus for example of the stem cells and the x-ray contrast agent. Each biocompatible material possesses an average decomposition time which is used for this. In particular, the support or envelope element is formed from a polymer or a polyethyleneglycol or a polyacrylate or a polyoxide.

Advantageously for an x-ray contrast agent especially well suited for imaging the first substance contains iodine or barium sulfate.

According to a further embodiment of the invention the stein cells are formed from myoblasts (skeletal myoblasts). These have a particularly large number of advantages as regards a low risk of tumor, a low rate of cell rejection and good availability, as well as ethical advantages. Alternatively bone marrow stromal cells or embryonic stem cells or endothelial progenitor cells or stem cells from fat cells or fetal cardiomyocytes can be used.

Advantageously the first element is formed of ferric oxide or ferrous oxide.

BRIEF DESCRIPTION OF THE DRAWINGS

The invention and further advantageous embodiments according to features of the subclaims are explained in greater detail in the following on the basis of diagrammatically illustrated exemplary embodiments, without thereby restricting the invention to these exemplary embodiments. In which:

DETAILED DESCRIPTION OF THE INVENTION

Figure 1:
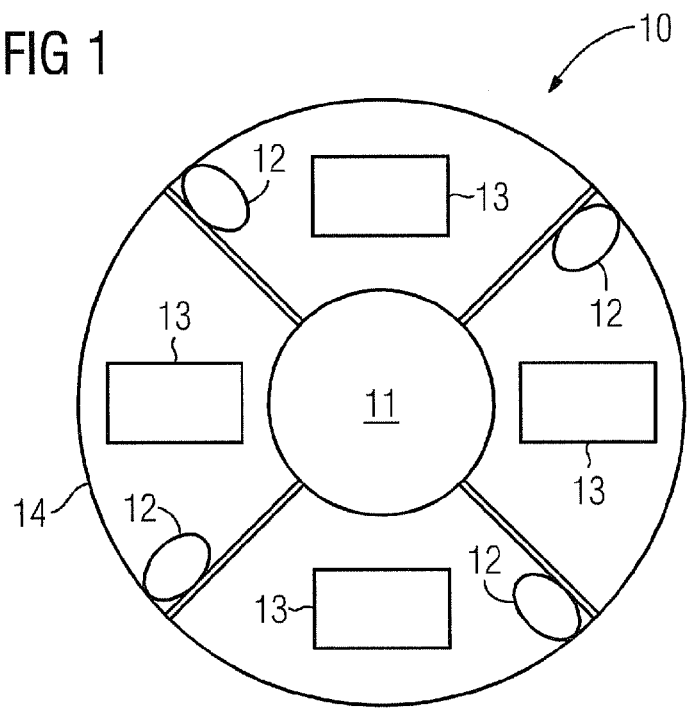
FIG. 1 shows a section through an inventive nanoparticle.

FIG. 1 shows an inventive nanoparticle 10, which has a magnetic core element 11, an x-ray contrast agent 13, stem cells 12 and an envelope 14. The magnetic core element 11 is for example arranged in the center of the nanoparticle 10 and is formed for example from ferric oxide ($Fe_2O_3$) or ferrous oxide ($Fe_3O_4$); other magnetic materials are also possible. The envelope 14 encloses in particular the core element 11 as well as the x-ray contrast agent 13 and the stem cells 12 and is embodied to be bioresorbable—in other words it dissolves in the body of a living being. To this end the envelope is for example found from a polymer or a polyethyleneglycol or a polyacrylate or a polyoxide. The x-ray contrast agent 13 possesses a low x-ray transparency and is preferably likewise biodegradable or at least eliminable. Iodine or barium sulfate can for example be used as an x-ray contrast agent. The nanoparticle has an average diameter of approximately 5 nm to 300 nm; preferably it is between 50 nm and 100 nm in size.

Figure 3:
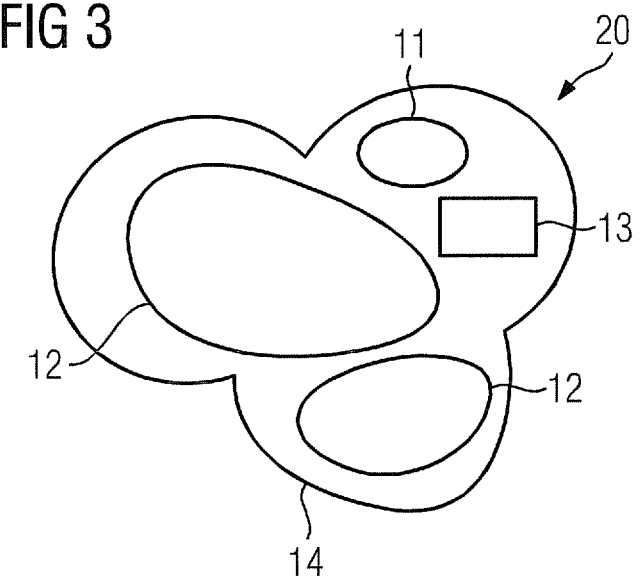
FIG. 3 shows an inventive group of nanoparticles.
Figure 4:
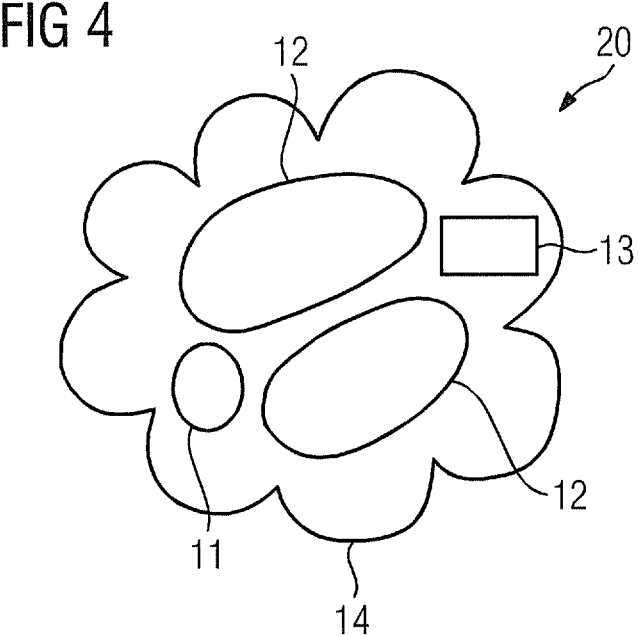
FIG. 4 shows a further inventive group of nanoparticles.

FIG. 3 and FIG. 4 show inventive groups or clusters 20 of at least three nanoparticles, having a magnetic core element 11, an x-ray contrast agent 13, stem cells 12 and an envelope 14. The magnetic core element 11 is arranged inside the group 20 of nanoparticles and is formed for example from ferric oxide ($Fe_2O_3$) or ferrous oxide ($Fe_3O_4$); other magnetic materials are also possible. The envelope 14 encloses the entire group/cluster of nanoparticles as a whole and also encloses the core element 11 as well as the x-ray contrast agent 13 and the stem cells 12 and is embodied to be bioresorbable—in other words it dissolves in the body of a living being. To this end the envelope is for example formed from a polymer or a polyethyleneglycol or a polyacrylate or a polyoxide. The x-ray contrast agent 13 possesses a low x-ray transparency and is preferably likewise biodegradable or at least eliminable. Iodine or barium sulfate can for example be used as an x-ray contrast agent. The group/cluster of nanoparticles has at least three up to a plurality of individual nanoparticles which can also contain several core elements.

The stem cells 12 are disposed undiluted or in a solution in the nanoparticle or group/cluster of nanoparticles and are embodied such that they can be used for angiogenesis or myogenesis. Angiogenesis means the introduction of body cells, in particular stem cells, into the coronary vessel system. In myogenesis body cells and in particular stem cells are injected directly into the myocardial muscle, advantageously in the region of the infarction scar, and there form new muscle cells which increase the pumping function of the heart.

What are known as skeletal myoblasts are particularly suitable for myogenesis. Skeletal myoblasts consist of precursor cells which lie in a quiescent state below the basal membrane of the muscle fibers. If the skeletal muscle is damaged the cell cycle is activated in these cells and the cells start to divide and mutate into functional muscle cells which heal the damaged skeletal muscle. Skeletal myoblasts can be extracted from the thigh for myogenesis, reproduced in bioreactors and injected into the patient's myocardial muscle. Myogenesis by means of skeletal myoblasts has a low risk of tumor and a low risk of rejection and the myoblasts are comparatively easy to obtain.

Alternatively to myoblasts (skeletal myoblasts) bone marrow stromal cells or embryonic stem cells or endothelial progenitor cells or stem cells from fat cells or fetal cardiomyocytes can also be used as stem cells.

A description of general stem cell therapy can be found in "Cell Transplantation for Myocardial Repair: Current Perspectives, Initial Experience in Humans, and Future Directions" by Chourmouzios Arampatzis et al., Euro PCR, 2004, pages 213-231.

Figure 2:
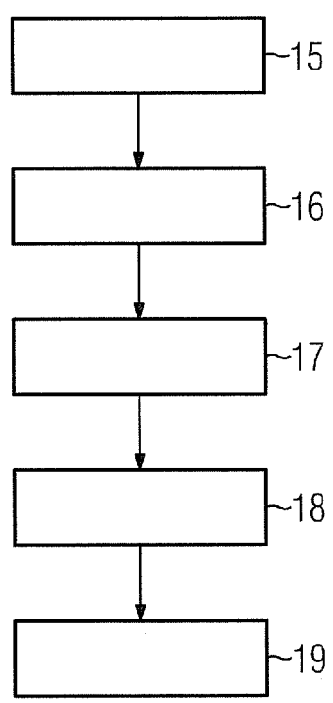
FIG. 2 shows a sequence of a method for stem cell therapy using nanoparticles.

FIG. 2 shows a method for positioning nanoparticles or groups/clusters of nanoparticles at a treatment location in a living being. Prior to the procedure the living being, in particular a patient, is generally placed on a patient table. As an optional first step 15 a diagnostic examination is performed using x-rays, for example a 3D angiography recording or a series of radioscopy recordings or a simple x-ray recording. Alternatively an ultrasound examination can also be performed. In a second step 16 a catheter which contains magnetic nanoparticles or groups/clusters of nanoparticles of the type described in the invention is introduced into the living being and positioned at a location intended for the treatment. The catheter can for example be introduced by effecting a venous entry and is pushed forward as far as the treatment location, for example an infarct region.

In a third step 17 the magnetic nanoparticles or groups/clusters of nanoparticles are injected into the living being. In a fourth step 18, which can also take place simultaneously with one of the previous steps, an externally generated magnetic field is focused on the treatment location such that the magnetic nanoparticles or groups/clusters of nanoparticles are held at the treatment location and in particular are concentrated still further. The nanoparticles or groups/clusters of nanoparticles are thereby held at the treatment location at least until the envelope of the nanoparticles or groups/clusters of nanoparticles has decomposed and the stem cells as well as the x-ray contrast agent are released. Advantageously one embodiment of the envelope entails the stem cells being diffused through the envelope. In this case the nanoparticles or groups/clusters of nanoparticles are held at the treatment location at least until the stem cells have diffused through the envelope. Then in an optional fifth step 19 a diagnostic examination can in turn be performed by means of x-rays, for example a 3D angiography recording or a series of radioscopy recordings or a simple x-ray recording, or alternatively an ultrasound examination can also be performed. The patient is then moved.

The invention can be briefly summarized as follows: for particularly effective stem cell therapy a nanoparticle or groups/clusters of nanoparticles, having a first element consisting of a magnetic material, a support or envelope element consisting of a biodegradable material, a first substance containing an x-ray contrast agent, and a second substance containing stem cells is provided, whereby the stem cells are embodied such that they can be used for angiogenesis or for myogenesis.

The invention claimed is:

1. A group of nanoparticles containing at least three nanoparticles, wherein each nanoparticle comprising:
    a first element consisting of a magnetic core element;
    a support element consisting of a biodegradable material;
    a first substance containing an x-ray contrast agent; and
    a second substance containing a stem cell to be used for angiogenesis or myogenesis,
    wherein the magnetic core element, the x-ray contrast agent and the stem cell are arranged inside the support element,
    wherein the support element is an envelope enclosing the first element, the first substance, and the second substance.

2. The group of nanoparticles as claimed in claim 1, wherein each nanoparticle has an average diameter between 5 nm and 300 nm.

3. The group of nanoparticles as claimed in claim 1, wherein the first substance comprises iodine or barium sulfate.

4. The group of nanoparticles as claimed in claim 1, wherein the stem cell comprises myoblasts.

5. The group of nanoparticles as claimed in claim 1, wherein the first element comprises ferric oxide or ferrous oxide.

6. The group of nanoparticles as claimed in claim 1, wherein the support element comprises a polymer, or a polyethyleneglycol, or a polyacrylate, or a polyoxide.

7. A method for positioning a group of nanoparticles, comprising:
    positioning a catheter containing the group of nanoparticles at an intended treatment location in a living being;
    injecting the group of nanoparticles into the living being; and
    arranging a magnetic field generated outside the living being in a region of the treatment location for holding the group of nanoparticles at the treatment location,
    wherein the group of nanoparticles comprises at least three nanoparticles,
    wherein each nanoparticle comprises a magnetic core element, a support element, an x-ray contrast agent, and a stem cell to be used for angiogenesis or myogenesis, and
    wherein the magnetic core element, the x-ray contrast agent and the stem cell are arranged inside the support element and are concentrated at the treatment location by the magnetic field until the stem cell is diffused through the support element,
    wherein the support element is an envelope enclosing the magnetic core element, the x-ray contrast agent, and the stem cell.

8. The method as claimed in claim 7, further comprising taking an x-ray recording before and/or after the injection of the group of nanoparticles.

* * * * *